(12) United States Patent
Nichols

(10) Patent No.: US 6,174,277 B1
(45) Date of Patent: Jan. 16, 2001

(54) THERAPEUTIC EQUINE MAGNETIC DEVICE AND METHOD

(76) Inventor: Wayne Nichols, 5003 County Rd 168, West Liberty, OH (US) 43357

( * ) Notice: Under 35 U.S.C. 154(b), the term of this patent shall be extended for 0 days.

(21) Appl. No.: 09/290,475

(22) Filed: Apr. 12, 1999

(51) Int. Cl.$^7$ ...................................................... A61N 1/00
(52) U.S. Cl. ................................................. 600/15; 54/82
(58) Field of Search ............................. 600/9–15; 54/82; 119/29, 96, 143

(56) References Cited

U.S. PATENT DOCUMENTS

| | | |
|---|---|---|
| 5,304,111 | 4/1994 | Mitsund et al. . |
| 5,389,061 * | 2/1995 | Nor .......................................... 600/15 |
| 5,426,925 * | 6/1995 | Smargiassi ............................. 600/15 |
| 5,453,074 | 9/1995 | Imoto . |
| 5,538,495 | 7/1996 | Ardizzone . |
| 5,782,743 | 7/1998 | Russell . |

FOREIGN PATENT DOCUMENTS

3205048 * 8/1983 (DE) ...................................... 600/15

* cited by examiner

Primary Examiner—John P. Lacyk
(74) Attorney, Agent, or Firm—Mark A. Navarre

(57) ABSTRACT

An improved technique for realizing the benefits of magnetic therapy in the field of equine care and treatment, in which a thin magnetic pad is positioned against the sole of a horse's hoof and a shoe fastened to the hoof sandwiches the magnetic pad between the hoof and shoe. Preferably, the magnetic pad is relatively thin, and the shoe is formed of a non-magnetic material such as aluminum. The pad and shoe may be separately applied, with the pad being temporarily held in place by an adhesive such as a quick drying rubber cement, or the pad may be bonded to the shoe and applied as a single item. The therapeutic effects of the magnetic pad are maximized because the shoe holds the pad in place, and the pad is maintained in contact with the hoof continuously, providing a simple and economical way of realizing the benefits of magnetic therapy.

9 Claims, 1 Drawing Sheet

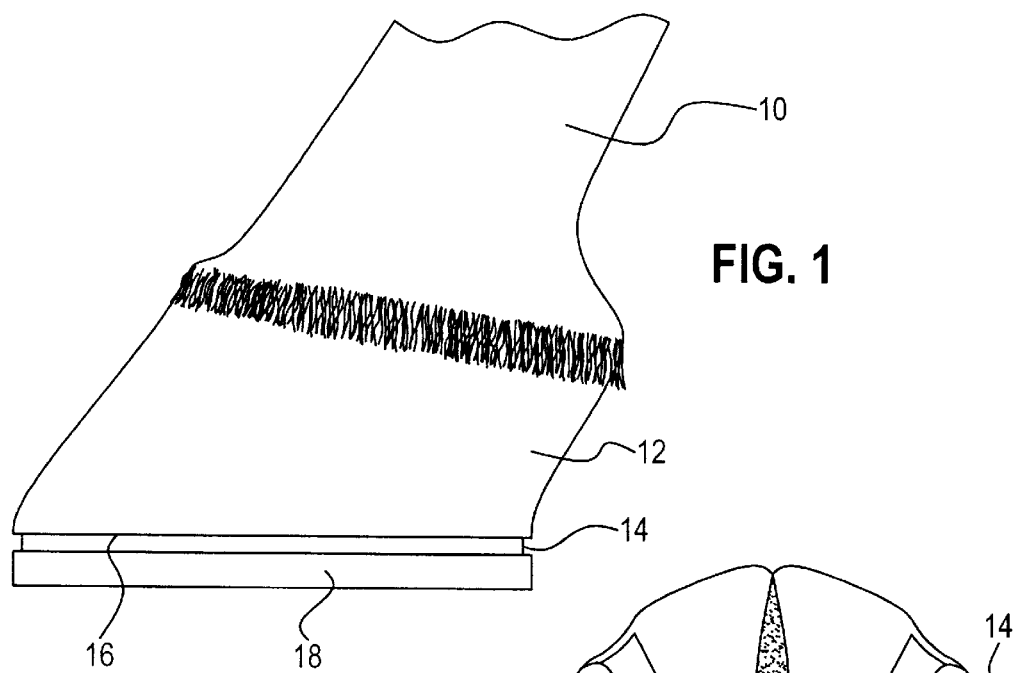
FIG. 1
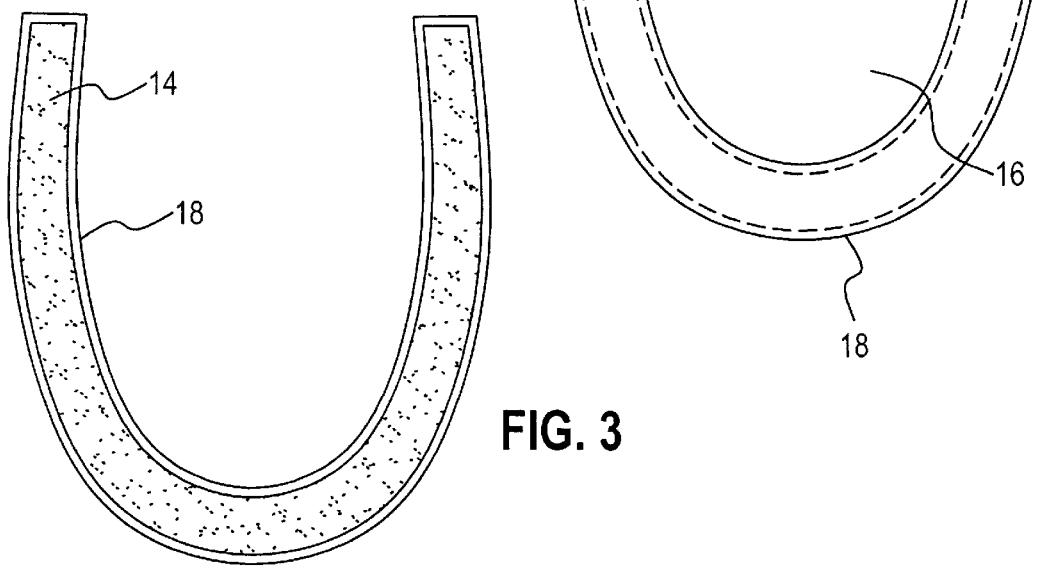
FIG. 2
FIG. 3

THERAPEUTIC EQUINE MAGNETIC DEVICE AND METHOD

FIELD OF THE INVENTION

This invention relates to the use of permanent magnetic materials for equine therapy.

BACKGROUND OF THE INVENTION

The therapeutic effects of bi-polar magnetic fields in both human and animal subjects are generally recognized in patent and other literature, particularly for the purposes of promoting healing and reducing stiffness and pain. In principle, the bi-polar magnetic regions produce magnetic fields that influence ionic fluids in the body, which tends both to produce warmth and improve circulation. The treatment is most generally carried out through the use of a pad or blanket of permanent magnetic material that has a regular repeating pattern of opposite polarity magnetic poles, such as produced by Nikken, Inc. of Los Angeles, Calif. See, for example, the U.S. Pat. No. 5,304,111, issued on Apr. 19, 1994, and incorporated herein by reference. Typically, the magnetic pad or blanket is wrapped or otherwise maintained in contact with the body, as for example in the U.S. Pat. No. 5,782,743, issued on Jul. 21, 1998, where elasticized bands retain and position magnetic pads in contact with a patient's elbow, knee, ankle, etc.

The field of equine care and treatment potentially presents a particularly useful application of magnetic therapy, particularly when racing is involved, because joint and muscle stiffness and injuries occur frequently, and prevent horses from achieving their top performance. Here, as with human therapy, it is known that healing and circulation can be improved by applying magnetic pads to the leg joints and muscles of a horse, but it is often difficult to properly position a pad and keep it in place for very long. Also, it is difficult to know where to position the pad for the best therapeutic benefit.

SUMMARY OF THE INVENTION

The present invention is directed to an improved technique for realizing the benefits of magnetic therapy in the field of equine care and treatment, in which a thin magnetic pad is positioned against the sole of a horse's hoof and a horse shoe fastened to the hoof sandwiches the magnetic pad between the hoof and shoe. Preferably, the magnetic pad is relatively thin, such as 0.125 inches, and the shoe is formed of a non-magnetic material such as aluminum (although a steel shoe may also be used). The pad and shoe may be separately applied, with the pad being temporarily held in place by an adhesive such as a quick drying rubber cement, or the pad may be bonded to the shoe and applied as a single item. Separate application of the pad and shoe is probably preferable in most applications since a worn shoe may be replaced without necessitating replacement of the magnetic pad. Of course, the pads may be applied to some or all of the hooves.

With the above-described technique, the therapeutic effects of the magnetic pads are maximized because the shoe holds the pad in place, and the pad is maintained in contact with the hoof continuously. This overcomes the difficulty involved with known techniques for manually applying magnetic blankets and pads, and provides a simple and economical way of realizing the benefits of magnetic therapy.

BRIEF DESCRIPTION OF THE DRAWINGS

The above and other advantages of the invention will become more apparent from the following description taken in conjunction with the accompanying drawings wherein like references refer to like parts and wherein:

FIG. 1 is a side view of a horse hoof, with a magnetic pad and shoe in place in accordance with this invention.

FIG. 2 is a bottom view of the hoof of FIG. 1, illustrating the magnetic pad and shoe, with a portion of the shoe shown in phantom.

FIG. 3 depicts an embodiment of this invention in which the magnetic pad is bonded to the shoe prior to being mounted on a hoof.

DETAILED DESCRIPTION OF THE INVENTION

FIG. 1 generally depicts the pastern 10 and hoof 12 of a horse's leg. As seen in FIGS. 1–2, the magnetic pad 14 is positioned in direct contact with the sole 16 of hoof 12, and a shoe 18 is positioned against the magnetic pad 14, sandwiching the magnetic pad 14 between the shoe 18 and sole 16. The magnetic pad 14 may be cut from a sheet of material having a regular repeating pattern of alternating polarity magnetic poles, such as produced and sold by Nikken, Inc. of Los Angeles, Calif., and preferably has a thickness of approximately 0.125 inches. The shoe 18 is preferably formed of aluminum or another non-magnetic material, so as not to influence the magnetic fields of the pad 14, but may be formed of a magnetic material such as steel, if desired. In either event, the shoe 18 is secured to the hoof 12 by nailing, per conventional practice.

According to a first embodiment, the magnetic pad 14 is secured to the sole 16 by an adhesive, which may be pre-applied to one surface of the pad 14, and the shoe 18 is subsequently secured by nailing. In this way, the shoe 18 may be changed without having to also change the magnetic pad 14. This may be particularly beneficial when aluminum shoes are used since the shoes may need to be changed several times before the magnetic pads 14 are damaged or worn out.

According to a second embodiment, illustrated in FIG. 3, the magnetic pad 14 is secured to the shoe 18 by bonding or gluing prior to nailing the shoe 18 to the hoof 12. With this approach, the pad 14 may be secured to the shoe 18 by either the shoe manufacturer or an individual user.

The present invention thus provides a convenient and low cost technique for realizing the benefits of magnetic therapy in the field of equine care and treatment. Since the shoe 18 protects the pad 14 and holds it in place, the pad 14 is maintained in continuous contact with the hoof 12, maximizing the benefits of magnetic therapy.

While the invention has been described in reference to the illustrated embodiment, it will be understood that various modifications will occur to those skilled in the art. For example, the magnetic pad 14 may be used with different sized shoes 18, such as a full shoe that covers the a large portion of the sole 16; this may be particularly beneficial in the treatment of foundering. Accordingly, it should be understood that magnetic therapy devices and methods incorporating these and other modifications may fall within the scope of this invention, which is defined by the appended claims.

The embodiments of the invention in which an exclusive property or privilege is claimed are defined as follows:

1. An equine magnetic therapy device, comprising:
    a sheet of magnetic material having a repeating pattern of alternating polarity permanent magnet poles formed at a surface thereof, such surface adapted to be placed in contact with a sole of an equine hoof; and a shoe adapted to be fastened to the equine hoof so as to sandwich the sheet of magnetic material between the shoe and hoof.

2. The magnetic therapy device of claim 1, wherein the sheet of magnetic material is secured to the hoof prior to fastening the shoe to the hoof.

3. The magnetic therapy device of claim 1, wherein the sheet of magnetic material is secured to the shoe before the shoe is fastened to the equine hoof.

4. The magnetic therapy device of claim 1, wherein the sheet of magnetic material has a thickness of approximately 0.125 inches.

5. The magnetic therapy device of claim 1, wherein the shoe is made of a non-magnetic material.

6. A method of equine magnetic therapy comprising the steps of:

positioning a sheet of magnetic material in contact with a sole of an equine hoof, the sheet having a surface in contact with the hoof having a repeating pattern of alternating polarity permanent magnet poles thereon; and fastening a shoe to the equine hoof so as to sandwich the sheet of magnetic material between the shoe and hoof.

7. The method of claim 6, including the step of:

securing the sheet of magnetic material to the hoof before fastening the shoe to the hoof.

8. The method of claim 6, including the step of:

securing the sheet of magnetic material to the shoe before fastening the shoe to the hoof.

9. The method of claim 6, wherein the shoe is formed of non-magnetic material.

* * * * *